United States Patent [19]

Shtabholz

[11] Patent Number: 4,987,885
[45] Date of Patent: Jan. 29, 1991

[54] LUMBAR TRACTION APPARATUS

[75] Inventor: Ludwig Shtabholz, Tel-Aviv, Israel

[73] Assignee: Meditrac LTD, Tel-Aviv, Israel

[21] Appl. No.: 227,142

[22] Filed: Aug. 2, 1988

[30] Foreign Application Priority Data

Dec. 2, 1987 [IL] Israel ........................................ 84695

[51] Int. Cl.⁵ .............................................. A61H 1/02
[52] U.S. Cl. ..................... 128/75; 128/78
[58] Field of Search ............... 128/75, 78, 69, 84 R, 128/89 R, 90, 92 V, 91 R, 90

[56] References Cited

U.S. PATENT DOCUMENTS

| | | | |
|---|---|---|---|
| 2,601,686 | 7/1952 | Roessler | 128/84 C |
| 2,835,247 | 5/1958 | Stabholz | 128/78 |
| 3,032,033 | 5/1962 | Ramirez | 128/90 |
| 3,420,230 | 1/1969 | Ballard | 128/84 R |
| 3,548,817 | 12/1970 | Mittasch | 128/78 |
| 3,889,664 | 6/1975 | Heuser et al. | 128/75 |
| 3,926,182 | 12/1975 | Stabholz | 128/78 |
| 4,057,056 | 11/1977 | Payton | 128/89 R |
| 4,166,459 | 9/1979 | Nightingale | 128/75 |
| 4,245,627 | 1/1981 | Mignard | 128/78 |
| 4,409,969 | 10/1983 | Will | 128/78 |
| 4,512,340 | 4/1985 | Buck | 128/90 |
| 4,708,130 | 11/1987 | Grudem | 128/89 R |
| 4,715,362 | 12/1987 | Scott | 128/75 |
| 4,721,102 | 1/1988 | Pethybridge | 128/78 |
| 4,809,685 | 3/1989 | Barnes | 128/74 |

Primary Examiner—Edgar S. Burr
Assistant Examiner—Huong Q. Pham
Attorney, Agent, or Firm—Charles E. Baxley

[57] ABSTRACT

A lumbar traction apparatus which includes a lower support attachable to a patient's pelvis and an upper support attachable to a patient's lumbar region. A pair of independent traction assemblies are provided with each spaced laterally from the other and each spanning between the supports. Each of the traction assemblies includes a vertically extending rod operatively connected to a raising mechanism housed in the lower support, with the traction assemblies serving to separate the supports thereby causing traction of the patient. Each of the raising mechanics are provided with a lever connected to the lower support and pivotable to raise incrementally a first plurality of thin metal caged plates on its rod with the plates being biased against a spring. Each of the raising mechanisms are provided with a release plate for enabling the patient to release traction thereof. When the raising mechanism is engaged it causes the upper support to slide up slowly on the rods thus producing the traction. Either side of the upper support can be raised separately to a different level, thus supplying differential traction. A lordosis pad is provided to be pressed against the patient's body.

14 Claims, 3 Drawing Sheets

LUMBAR TRACTION APPARATUS

BACKGROUND OF THE INVENTION

The invention relates to an improved lumbar traction apparatus designed for improved and more comfortable treatment of low back disorders of disc origin, as well as treatment of patients suffering from dorso-lumbar scoliosis and some vertebral fractures.

Several designs of lumbar traction devices have been described in the prior art including such devices developed by this inventor.

One such apparatus is described in U.S. Pat. No. 2,835,247, based on Isreal Patent Application 10691, wherein an apparatus includes a pair of curved steel bars strapped to a patient, so that a bottom one of the bars rests on the iliac crests of the patient and is not movable; the top one of the bars is situated at 8-9 Th level and is movable. The straps are pulled tight, and a pair of spaced traction control assemblies extending between the supports are operated separately by moving the upper support upwards thus separating the patient's thorax from his pelvis.

A problem with said device is mechanical difficulty in turning a handwheel and locking the wheel in place once traction has been achieved. The physical location of the handwheel makes it impossible for the patient to apply traction by himself, thus precluding the device from being used for self treatment. The strap designs are such that they are difficult to handle and tighten securely. The metal bars are heavy, and if x-ray is required during traction, it can not be performed feasibly, because the rays will not go through metal.

Another more modern apparatus is described in U.S. Pat. No. 3,926,182, based on Isreal Patent Application 41411 wherein the apparatus includes a pair of upper and lower rigid U-shaped supports attached to the upper and lower waist portions of a patient. A belt assembly associated with each of the supports is used for tightening to the patient. Two traction assemblies are spaced apart, extending between the supports, having a vertically extended tube connection and a tooth rod mounted telescopically, and a rotable shaft carrying a pinion engaged with teeth on the rod which is driven by a ratchet drive mechanism associated with the end traction control assembly. When the ratchet drive is rotated, it rotates the shaft carrying the pinion in one direction thus moving the rod relative to the tube, thereby causing traction in the lumbar region of the patient.

The traction power can be measured and visualized by a gauge provided on the upper support. The device is also provided optionally with a lordosis pad assembly mounted externally on the lower support, enabling control of forward convexity of the patient's spine.

The supports are metallic (steel) and are padded by foam padding covered by PVC or other suitable cover material. The belt assembly is similar to an automatic seat belt strap, tightened by ratchet drive mechanism mounted on each of the support's ends.

The disadvantage of said system is that due to the metal pieces in almost each part of the device one can not use x-ray or CT control during traction.

The traction assembly mechanisms, and the lordosis pad mechanism are mounted externally on the supports, thus causing disturbance to the patient's free movement. The belt tightening assembly is cumbersome and awkward to apply. Further, the system does not enable the user to apply differential traction as the teeth mechanism of both traction drive ratchet mechanisms always go up to the same level. The possibility of applying differential traction has great importance in the treatment of patients with sciatic scoliosis and scoliotic patients. The lordosis pad provided in the apparatus can only be moved along a fixed track by slow movement of a screw, and only at a preset position on the back, which therefore limits its use, and for achieving a desirable lordosis enlargement too much time must be spent.

SUMMARY OF THE INVENTION

It is a purpose of this invention to provide solutions to the above mentioned drawbacks (of the prior art designs), and introduce several innovations in design and structure of the prior art devices thus providing an improved apparatus, enabling the treatment of not only back disorders of disc origin, but also providing treatment for scoliosis patients, and patients with some vertebral fractures; as well as self treatment in chronic cases and as prophylactic measure. The new invention also provides for an apparatus which can be manufactured cheaply in large scale production lines.

The apparatus hereby provided is made mostly of plastic reinforced materials, padded with flexible polyurethane foam, thus enables use of x-ray or CT control during treatment.

The apparatus is lighter in weight, hence easier to carry by the patient.

The lumbar traction apparatus hereby provided comprises; a pair of U-shaped adaptable supports to be attached to the patient under treatment; said supports are constructed from reinforced plastic bars positioned in a flexible polyurethane foam casting serving as a padding; and said supports having each a plurality of pinned free moving links equally spaced at both ends, enabling supports to be fitted to any required measure of a patient undergoing treatment; and having a belt assembly associated with each of the supports for tightening them to the patient; said belts having each a mechanism to enable tightening of said supports to a requested position by moving a handle placed in the middle; and having a pair of laterally spaced apart traction control assemblies extending between said supports, each assembly having a vertically extended rod connected to the top support into a housing, cast into said polyurethane foam; said housing containing a spring through which said rod passes, and said spring operating a gauge arm mounted on rod end measuring the traction power; and the other end of the rod is connected to a raising mechanism housed in the said polyurethane foam cast of the lower said support; said raising mechanism is operated by a lever raising a plurality of thin metal stacked plates caged on the said rod pressed down by a spring in the lower section of said housing; through a second group of such thin caged plates placed at an angle, on the same rod, pressed by another spring in the upper section of said housing; and having a release plate projected out of the housing enabling the user to release said rod and slide it back to a lower position; when said lever is applied the raising mechanism causes the upper support to slide up slowly on said rod thus causing traction; each upper support side can be raised separately, and to a different level thus applying differential traction; and having a plate secured to both of said traction assembly rods, extending across the patient's back, between the two said supports, having a pad assembly positioned in any part of said extended plate, to be pressed toward the patient's body and remain in such a pressed position for a desired period for applying a horizontal force; and having a track cast into the middle of said lower support, also for positioning of said lordosis enlarging pad.

DESCRIPTION OF THE DRAWINGS

An embodiment of the invention is illustrated by way of example in the accompanying drawings.

DESCRIPTION OF THE INVENTION

Figure 1:
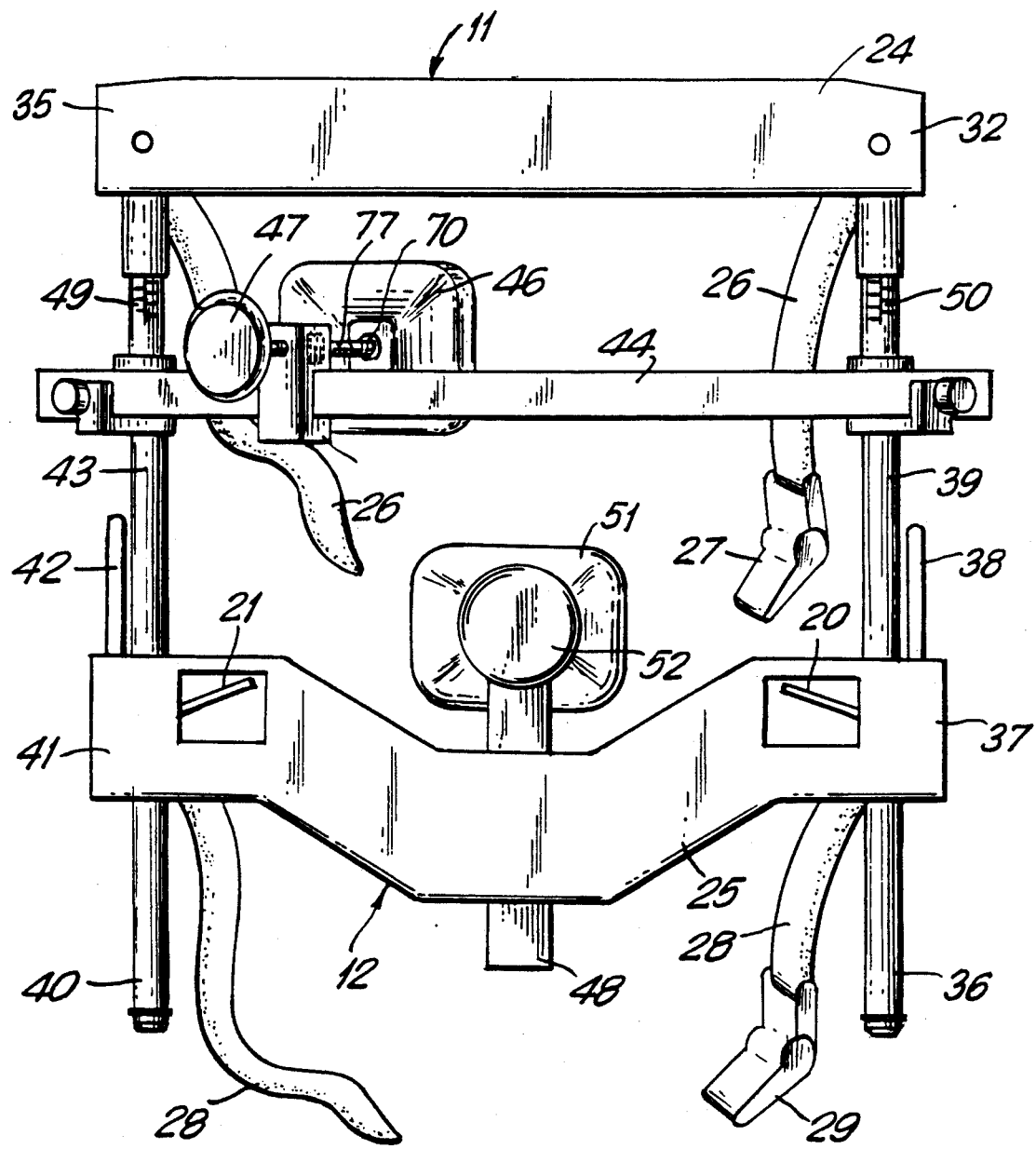
FIG. 1 illustrates a general assembly view of the device seen from the back of the patient, when belts are unstrapped.

Referring now to FIG. 1 illustrating the traction apparatus.

The apparatus comprises a pair of upper and lower U-shaped supports 11, 12 shown attached to the waist of a patient undergoing treatment. The supports have internal reinforced plastic bars casted into flexible polyurethane foamed plastic bars casted into flexible polyurethane foamed padding 24, 25.

The ends of the supports have two pairs of pinned free moving links not shown. Strapping belts extended from each of the supports ends 26 for the upper support, and 28 for the lower support. The belts and buckles 27, and 29, and tightening mechanisms not shown which are tightened on the patient's front middle.

The traction control assemblies shown on both sides 43 and 39 having the two upper housings 32 and 35 casted into the polyurethane foam of the supports, having two gauges for measuring traction power applied 49 and 50. The rods 36, 40 extend between supports 11 and 12, and go through housings 37 and 41 cast into lower support polyurethane foam 37 and 41 are the plate lifting mechanisms operated by hand levers 42 and 38 extending out of the polyurethane casting which when applied cause traction forces between the supports when they move up to the rods 40, 36. Differential traction can be applied when one mechanism (41 or 37) is moved up and the other remains static.

Release plates 20, 21 extending out of housings 41, 37 release the traction force and allow housings to move down the rods 36, 40 respectively. Bar 44 extends between rods 36, 40 and is secured to them, and the pad mechanism 47 can be fitted into any position along the bar 44, the lordosis pad 47 having a pressing knob 46. A second pad mechanism is placed at the centre of the lower support 12, on the track 48, having also a pad 51 pressed by a knob 52.

Figure 3:
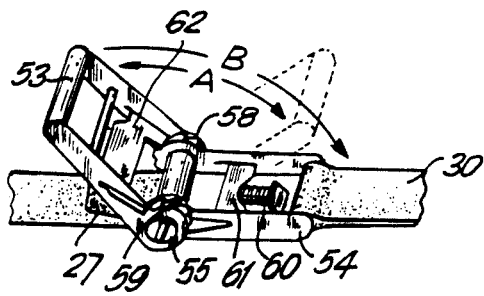
FIGS. 2 and 3 illustrate the belt tightening mechanism.
Figure 2:
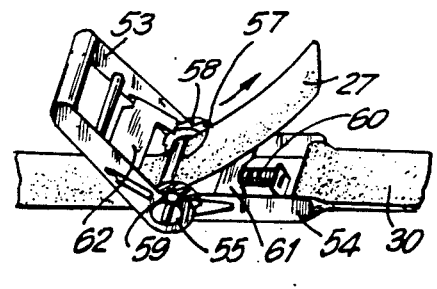

FIGS. 2 and 3 illustrate a tightening mechanism applied by a patient in the middle of his front (near the stomach area). Buckles 53 and 54 are mounted on pinion 55 having a central slit 57 through which one of the belt ends 27 is passed and rolled backwards. The other belt end 30 is secured to 54 as shown. The ratchet wheels 58, 59 are mounted on pinions 55, and spring 60 presses plate 61 and allows movement of buckle 54 in one direction only. Plate 62 is secured by a spring (not shown) allowing buckle 53 to move in one direction only along teeth of ratchet wheels 58, 59. When buckle 53 is moved from position A to B (as shown in FIG. 3) belt end 27 moves through slit 57 and tightens onto the patient's body.

Figure 4:
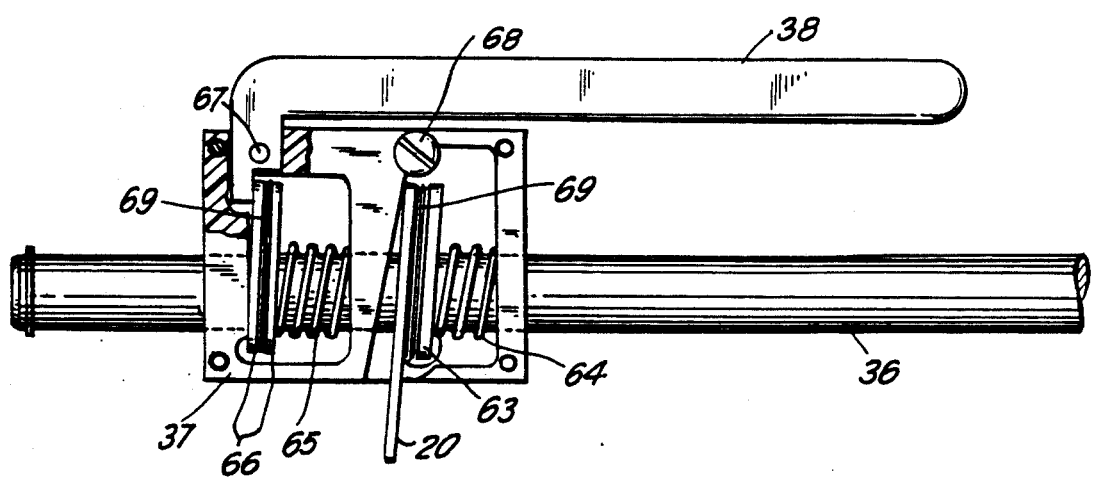
FIG. 4 illustrates the traction assembly.

FIG. 4 illustrates the detail of the traction control mechanism assembly. The rod 36 extends between upper housing 32 (not shown here) and lower housing 37. Lever 42 secured to the housing 37 by screw 67 rests on one of two steel plates 66, which are pressed down by spring 65.

Thin caged plates 69 (about 11) are placed between plates 66, and between plate 63 and release plate 20 in upper section of housing 37. Screw 68 sets the angle of release plate 20, and spring 64 presses plate 63 and caged plates 69 on to release plate 20.

When lever 42 is raised plate 66 is moved, moving with it the caged plates 69 (mounted on rod 36), the friction applied by the plates caged on the rod 36 cause the rod to slide through the second set of caged plates in the upper part of the housing, thus lifting the housing upwards towards housing 32 (not shown). When release plate 20 is pulled, the caged plate 63 releases the rod 36, and the housing moves downward.

Figure 5:
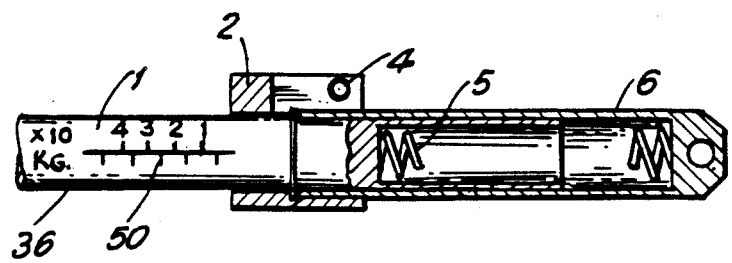
FIG. 5 illustrates the detail of the traction power gauge.

FIG. 5 illustrates the upper housing and traction power gauge mechanism. The upper hollowed housing 6 (cast into polyurethane foam of upper support 32 not here shown) the rod 36 end is marked with FIGS. 50 illustrating the applied traction power as shown in FIG. 1. The rod 36 is wound by a spring 5 at the end fitted into the housing 6 and pressing the rod end away from the housing, spring 5 bears on box 2 mounted on the rod telescopically, and secured by screw 4, so that when rod 36 is pressed by raising the mechanism into housing 6, spring 5 is compressed and pushes box 2 along the rod onto marked section 1 which thus gauges the force applied by the rod 36 on to spring 5.

Figure 7:
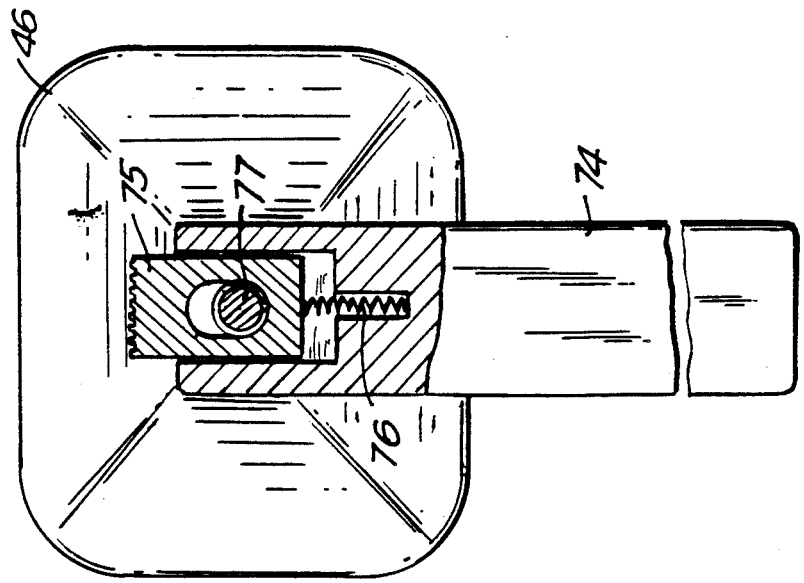
FIGS. 6A, 6B, and 7 illustrate a detail of the lordosis pad assembly.
Figure 6B:
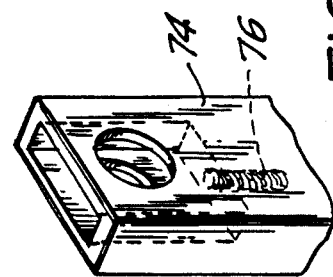
Figure 6A:
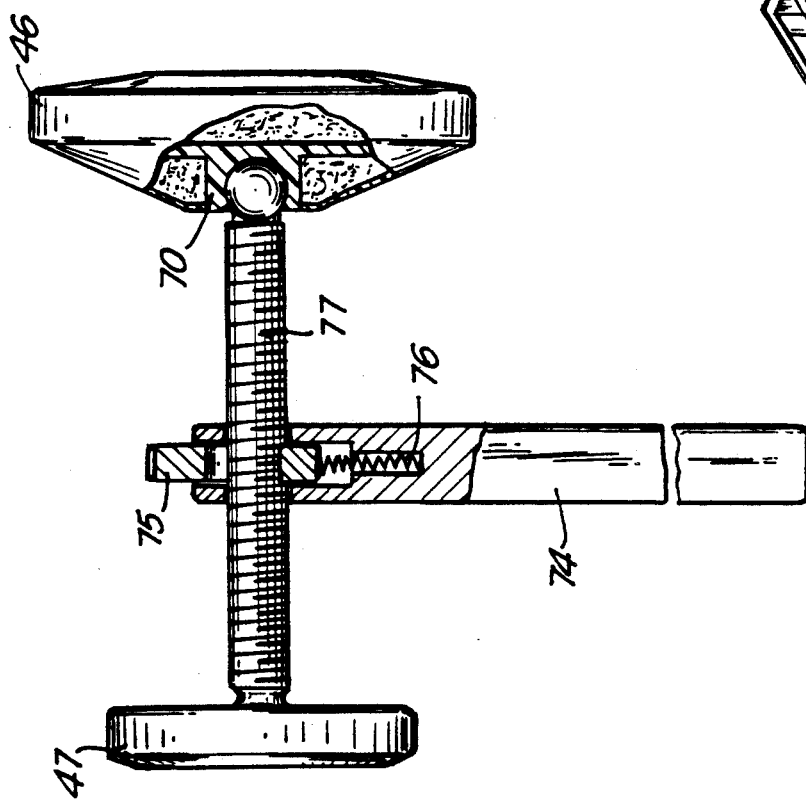

FIGS. 6A, 6B, and 7 illustrate the lordosis pad mechanism. The pad 46 is mounted on a steel (or reinforced plastic) plate 70, and plate 70 is connected by a ball connection to a screw pin 77, having on the other side a knob 47. A hollowed plate 74 is mounted telescopically on central part of screw pin 77. The pin 77 passes through a bored passage in plate 74 in the form of a lower half screw and an upper elliptical enlarged hole. A further steel plate 75 fitted into hollowed plate secured to the screw pin 77 by spring 76, having the same shaped bore as plate 74. When knob 47 is pressed in pad 46 is pressed towards the patient's body, when pressure on knob is released, spring 76 presses up plate 75 which latches screw-pin 77, and prevents it from moving backward away from the patient. To release the pressure, plate 75 is pressed down (against spring 76) and the screw pin can move freely backward to release the pad's pressure. FIG. 7 shows the cross section of plate 74 and 75, with spring 76 action on plate 75.

In a preferred embodiment of the lower U-shaped support is curved downward at its centre, and said lordosis pad's track is secured in the polyurethane foam padding at the centre of the curve. This arrangement enables positioning of the lordosis pad when both supports are mounted close to each other.

In the preferred embodiment the gauge measuring the traction power is mounted directly on a traction rod assembly extending out the housing cast into the upper support, and secured into the housing by a spring (see FIG. 5).

In the preferred embodiment the lordosis pad mechanism has the following design: A pad mounted on a bar (steel or preferably reinforced plastic), the bar is mounted on a screw-pin by a ball joint, and having on the other end a pressure knob.

A hollowed plate is mounted telescopically on the central part of the screw pin having a bored passage for the pin in the form of a lower half screw and an upper ellipsoidal enlarged half hole; and having a further steel plate fitted into the hollowed plate secured to the screw pin by a spring placed inside the hollowed plate and having the same shaped bore. So that when the pad is placed in position on the track, or onto the curved plate described above, and the pressure knob is pressed towards the body, the screw passes freely through the bored plates until the required pressure is achieved. When the knob is released, the spring in the hollowed plate passes down the inner plate, which locks passage by the half screw bore engaging with the screw. To release the pad's pressure the inner plate must be pressed up slightly (against the spring's force) thus releasing the screw passage, and releasing the pad (see FIGS. 6A, 7).

The two support inner bars, and the plate carrying the lordosis pad could be constructed of a reinforced plastic material such as a composite of epoxy resins reinforced by either fiber glass or carbon fibers, or a composite of unsaturated polyester resins reinforced by fiberglass or glass fibers matt; or any reinforced thermoplastic material produced by any conventional technique such as extrusion or injection molding. This construction enables x-ray penetration through the supports when the device is carried by a patient.

The traction assembly could be made of steel, but should preferably be made from reinforced plastics or composites, especially the two housings and central rod. This construction will greatly reduce the weight of the device, and avoid interference during x-rays or CT control.

The lordosis pad mechanism could also be made of steel, but should preferably be of reinforced plastic, so that x-ray and CT control can be applied.

In cases of some vertebral fractures having no neurological complications, said lumbar traction apparatus can be used for reposition of the dislocated vertebral fracture; before casting the plaster of Paris, using the enlarging lordosis pad mechanism provided. Horizontal force is then applied. When using a plastic made lordosis pad one can reconfirm position of said vertebral fracture correction by x-ray or CT. The plaster of Paris cast is then applied, leaving in the cast the inner part of the lordosis pad so that pressure could be applied occasionally thus decreasing substantially the number of collapses of the vertebral fractures while the patient is still in the cast.

In the preferred embodiment the belt strapping tightening mechanism operates as follows:

Two metal buckles are connected onto a central common hinge pinion, having on both ends security locking ratchet wheels secured to the said pinion by rivets. The said buckles having spring located ratchet pin mechanisms forcing the pins towards the pinion and a wheel allowing the buckles to move only in one direction.

When one of the belt's ends is secured to one of said buckle ends, and the other belt end is passed through a slit in the centre of said pinion, and any of the buckles is moved towards the other with the free movement of the ratchet wheel the mechanism pulls in the belt (through the pinion slit) not allowing return passage of the belt, thus causing tightening. To release the belts one pulls the buckles apart, thus allowing passage of the belt through the slit. (see FIGS. 2 and 3).

I claim:
1. A lumbar traction apparatus comprising in combination:
   a pair of U-shaped supports each including an upper and a lower support each constructed from plastic bars cast in polyurethane foam which serves as padding;
   each of the supports provided with a belt assembly for engaging it about a patient and each of the supports having a handle positionable at the front middle of the patient;
   each of said belt assemblies provided with tightening means for tightening it and operable by moving its associated handle;
   a pair of laterally spaced traction assemblies each spanning the patient's lumbar region between said supports, with each of the traction assemblies provided with a vertical rod having an upper end connect to the upper support;
   each of said traction assemblies provided with a spring connected between its associated rod and the upper support, and each of the springs provided with a gauge for measuring traction;
   each of the rods having a lower end connected by adjusting means to the lower support;
   each of the adjusting means comprising a first set of plurality of thin metal caged stacked plates, a spring, a lever organized to engage said first plurality of thin metal caged stacked plates about its associated rod, with the stacked plates retained by said spring that abuts against the lower support, whereby when said levers are engaged the stacked plates causes its associated rod to be raised relative to the lower support thus increasing the distance between the upper support and lower support thus causing traction of the patient;
   each of the adjusting means provided with a second set of plurality of thin metal caged stacked plates and a release plate projecting out of the lower support, each of said release plates is connected to its respective plurality of thin stacked plates to engage or disengage them from its associated rod;
   a bar spanning across the patient's back between said rods with a lordosis pad connected to the bar, and pressing means for pressing the lordosis pad against the patient's back to apply localized force thereagainst.

2. The lumbar traction apparatus according to claim 1 further characterized by the bars being made of a material which is transparent to X-ray and CT.

3. The lumbar traction apparatus according to claim 1 further characterized in that said bars are made of epoxy resin reinforced by glass fibers.

4. The lumbar traction apparatus according to claim 1 further characterized in that said bars are made of of polyester resin reinforced by glass fibers.

5. The lumbar traction apparatus according to claim 1 further characterized by the bars being made of a reinforced thermoplastic material made by injection moulding.

6. The lumbar apparatus according to claim 1 further comprising gauges being mounted on the upper housing.

7. The lumbar traction apparatus according to claim 1 further characterized by said traction assemblies and lordosis pad made of reinforced plastic material.

8. The lumbar traction apparatus according to claim 1 further characterized by the lordosis pad being mounted on a socket which engages pivotally about a ball mounted on a threaded shaft, the shaft passing telescopically through a sleeve into which it screwably engages, the sleeve connected fixedly to an arm mounted on the bar, the shaft having an end remote from the pad with a knob thereon for rotating the shaft and thereby engaging or disengaging the pad, the arm defining a chamber with a latch therein, a spring connected between the arm and the latch to urge the latch from a first position to a second position, the latch provided with a hole through which the sleeve passes, the latch provided also with a projection extending out of the arm whereby the projection can be pressed to move the latch from the second position to the first position, the sleeve having an opening through which the latch is passable to engage the shaft; in the first position the latch engaging the shaft to lock the pad in a desired position; in the second position the latch being out of engagement from the shaft so that the position of the pad can be changed by turning the knob.

9. A lumbar traction apparatus comprising in combination:
a lower support attachable to a patient's pelvis and an upper support attachable to the patient's lumbar region,
a pair of independent traction assemblies spaced laterally from each other and each spanning the supports,
each of said traction assemblies having a vertically extending rod operatively connected to a raising means housed in the lower support to separate the supports causing traction of the patient,
each of said raising means provided with a first set of plurality of thin metal caged stacked plates, a first spring biased against said plates, a lever connected to the lower support, each of said levels engages its associated thin metal caged stacked plates and said rod causing said rod to be raised relative to the lower support thus causing traction of the patient;
each of said raising means provided with a release plate projecting out of the lower support and operatively connected to a second set of plurality of thin metal caged stacked plates for enabling the patient to release one of said rods from engagement with said plates.

10. The lumbar traction apparatus according to claim 9 further characterized by said second set of plurality of thin metal caged plates is placed at an angle on said rod and biased against a second spring, said release plate connected to said second plurality of plates for controlling their orientation relative to said rod.

11. The lumbar traction apparatus according to claim 10 further characterized by said rod of each of said assemblies extending into a recess formed in said upper support, a spring in said recess through which its associated rod passes, said spring arranged to bias a gauge operatively connected to the rod for measuring traction.

12. The lumbar traction apparatus according to claim 9 further characterized by a bar connected to both of said rods and extending across the patient's back, a lordosis pad mounted on said bar and arranged for engagement against the patient's body.

13. The lumbar traction apparatus according to claim 9 further characterized by the supports made of reinforced plastic bars positioned in a flexible polyurethane foam casting which serves also as padding, said supports further provided with means for enabling the supports to be fitted to any required conformation of a patient.

14. The lumbar traction apparatus according to claim 9 further characterized by a belt assembly operatively associated with each of the supports for tightening it to the patient, each of said belt assemblies having a mechanism for tightening it to the patient to a desired position by the patient moving a handle located at the patient's front center.

* * * * *